United States Patent [19]

Moore et al.

[11] Patent Number: 5,240,586
[45] Date of Patent: Aug. 31, 1993

[54] RADIATION-SENSITIVE COMPOSITION AND USE THEREOF IN THE PREPARATION OF ELECTROCHEMICAL ION SENSORS

[75] Inventors: Christopher P. Moore, Harrow; Malcolm D. Purbrick, Bushy; Derek A. Thomason, Waterford; Kevin J. Parr, Harrow, all of United Kingdom

[73] Assignee: Eastman Kodak Company, Rochester, N.Y.

[21] Appl. No.: 475,510

[22] Filed: Feb. 6, 1990

[30] Foreign Application Priority Data

Apr. 26, 1989 [GB] United Kingdom ............. 8909561

[51] Int. Cl.$^5$ .......................................... G01N 27/26
[52] U.S. Cl. .............................. 204/418; 252/500; 252/518; 252/521
[58] Field of Search .................. 204/418, 180.6; 252/500, 518, 521

[56] References Cited

U.S. PATENT DOCUMENTS

| | | | |
|---|---|---|---|
| 4,352,725 | 10/1982 | Sugano et al. | 204/195 M |
| 4,592,816 | 6/1986 | Emmons et al. | 204/415 |
| 4,906,376 | 3/1990 | Fyles | 204/418 |
| 4,921,591 | 5/1990 | Mochizuki et al. | 204/418 |

OTHER PUBLICATIONS

Light-Sensitive Systems, Jaromir Kosar, (1965) pp. 158–163.
Ledwith, A. and Purbrick, M. D., Polymer, vol. 14, (1973, pp. 521–522.
Wagner, H. M. and Purbrick, M. D., The Jorunal of Photographic Science, vol. 29, (1981), pp. 230–235.

*Primary Examiner*—John Niebling
*Assistant Examiner*—Bruce F. Bell
*Attorney, Agent, or Firm*—Robert Luke Walker

[57] ABSTRACT

Radiation-sensitive compositions are disclosed of a type suitable for preparing ion sensitive membranes for electrochemical ion sensors. The compositions are comprised of a radiation-sensitive polymer containing radiation-sensitive recurring units having an ionophore group and recurring units having a crosslinking group. In preparing a membrane the radiation-sensitive composition is coated onto a sensor, exposed to activating radiation to produce crosslinking in areas where the membrane structure is desired, and removed in any remaining non-exposed areas.

11 Claims, 2 Drawing Sheets

RADIATION-SENSITIVE COMPOSITION AND USE THEREOF IN THE PREPARATION OF ELECTROCHEMICAL ION SENSORS

FIELD OF THE INVENTION

The invention relates to a radiation-sensitive composition particularly suitable for use in the preparation of an ion-sensitive membrane for an electrochemical ion sensor.

BACKGROUND

A great variety of electrochemical sensors utilizing an ion-sensitive membrane for the measurement of various ions in solution are known. In general terms, the ion-sensitive membrane contains a compound which interacts with the ions of interest. By the appropriate use of the sensor as an electrode, an electrical effect resulting from the interaction of the ions with the membrane can be measured to provide an indication of the activity of the ions in solution. If the membrane interacts selectively with a particular ion, the sensor may be described as ion-selective rather than ion-sensitive.

Examples of electrochemical sensors include those based on an underlying silicon structure such as microelectronic field effect sensors in which the gate region of the sensor is covered with an ion-sensitive membrane. Such sensors require the precise deposition of an ion-sensitive membrane over a very small surface area.

U.S. Pat. No. 4,352,726 describes the preparation of field effect sensors wherein the ion-sensitive membrane is produced by depositing a polymer containing a macrocyclic ionophore over the surface of the sensor. It specifically describes coating the sensor with an epoxytype polymer which is subsequently cured for many hours. Superfluous hardened polymer has to be removed by ion etching so that only the gate region of the sensor is covered by the membrane.

SUMMARY OF THE INVENTION

The invention provides a radiation-sensitive composition suitable for preparing ion-sensitive membranes which offers advantages having regard to the method described in U.S. Pat. No. 4,352,726. In particular, the composition provides crosslinking in response to activating radiation. The coated polymer can be imagewise exposed to activating radiation to provide rapid formation of a crosslinked membrane precisely where it is required. The unexposed and, therefore, uncrosslinked polymer can be easily removed by solvent.

The invention provides a radiation-sensitive composition comprising a radiation-crosslinkable polymer wherein the polymer comprises recurring units having an ionophore group and recurring units having a crosslinking group.

The invention also provides a method of preparing a crosslinked ion-sensitive composition which method comprises exposing a radiation-sensitive composition of the invention to activating radiation. The crosslinked composition may be in the form of a membrane for an electrochemical sensor.

In a particular aspect, the invention provides a method of preparing an electrochemical sensor having an ion-sensitive membrane which method comprises coating a surface of the sensor with a radiation-sensitive composition of the invention, exposing to activating radiation the area of the coated surface where the membrane is required in order to crosslink the composition in that area and removing any non-exposed portions of the composition from the surface.

BRIEF DESCRIPTION OF THE DRAWINGS

The invention is further illustrated with regard to the accompanying drawings wherein.

DESCRIPTION OF PREFERRED EMBODIMENTS

Figure 1:
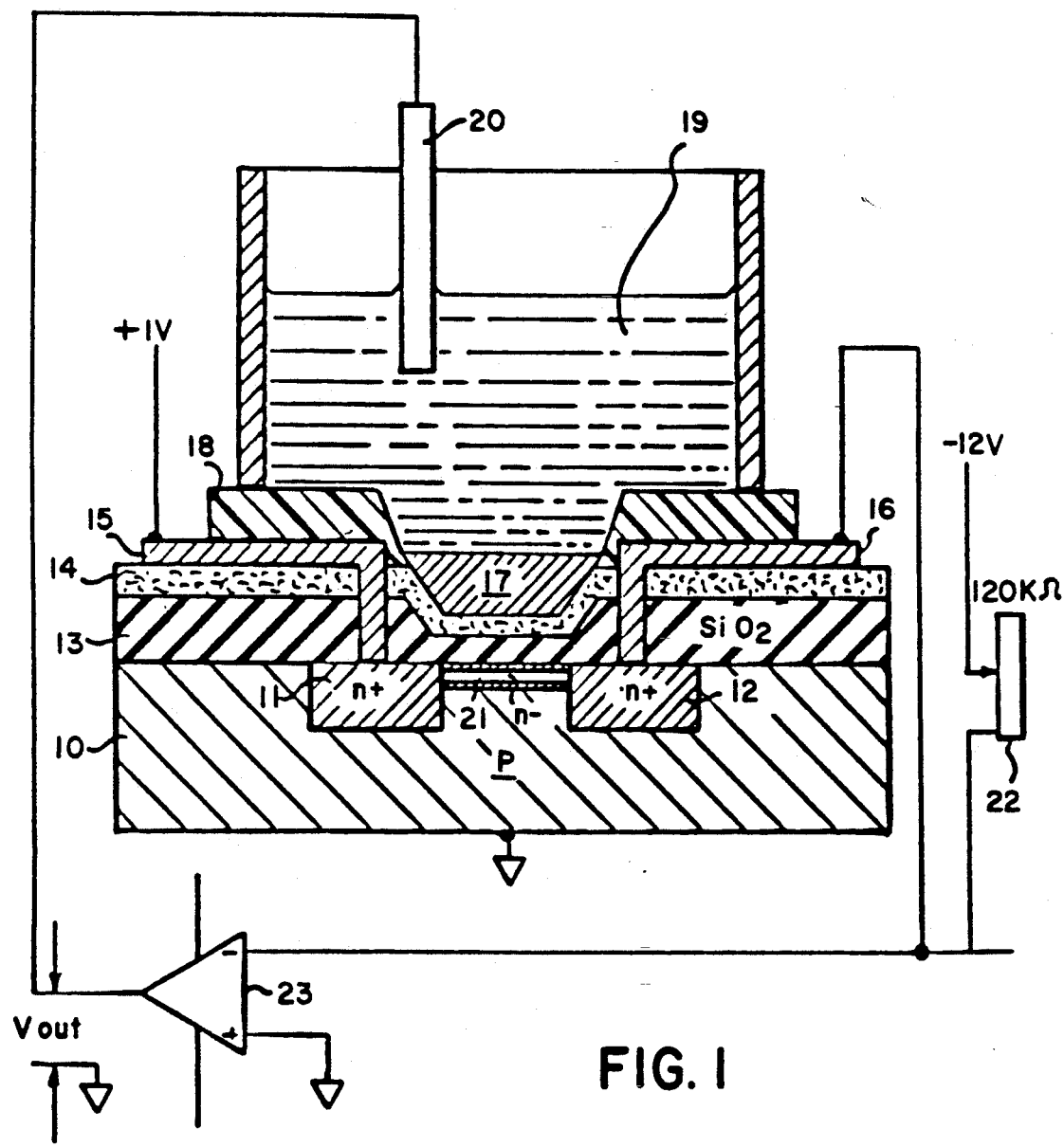
FIG. 1 is a schematic view of an ion-sensitive field effect transistor (ISFET) of the invention in use.

The radiation-crosslinkable polymer may be capable of being crosslinked directly by the action of activating radiation. For example, the crosslinking group may be a photoactivatable group, e.g., a cinnamate group. Alternatively, the polymer may require the presence of a photoactive crosslinking initiator to initiate the crosslinking reaction.

In one preferred embodiment of the invention the crosslinking group is a nucleophilic group and the composition contains a radiation-sensitive transitional metal carbonyl compound.

Examples of suitable nucleophilic groups include epoxy, carboxyl, hydroxy, tertiary amino, morpholino, unsaturated nitrogen-containing heterocycle and mercapto groups. Suitable transition metal carbonyl compounds include those described in U.K. Specification No. 1,463,816. These include toluene-aniline- and mesitylene-chromium tricarbonyl, dimanganese decacarbonyl and molybdenum hexacarbonyl. Benzene chromium tricarbonyl is particularly preferred because of superior photographic speed and availability. Further information regarding the use of transition metal carbonyl compounds as crosslinking initiators may be found in U.K. Specification No. 2,106,522.

In another preferred embodiment of the invention the crosslinking group is an ethylenically unsaturated group and the composition contains a photopolymerization initiator. Many photopolymerization initiator systems are known. For example, a single aromatic carbonyl initiator may be used, e.g., benzoin, benzil or acetophenone. A particularly preferred initiator system is a coinitiator composition comprising an aromatic carbonyl compound and a tertiary amine. The combination of a ketocoumarin e.g. 3,3'-carbonyl-bis(5,7-di-n-propoxycoumarin) and an amine e.g. N-phenylglycine is particularly favored.

Preferably, a chain of from 4 to 15 atoms separates the crosslinking group from the backbone of the crosslinkable polymer, The chain may comprise an alkylene group. A particularly preferred chain comprises an alkylene group having from 2 to 10 carbon atoms in combination with a connective moiety, such as a carboxy, —C(O)O—, or amido, —C(O)NH—, moiety, The ionophore may be selected from the large number of ionophores known to be suitable for use in ion-sensitive electrodes. It may form part of a monomer used to prepare the crosslinkable polymer or it may be reacted with a crosslinkable polymer. The ionophore can be incorporated in the monomer or the polymer by conventional synthetic modifications. Examples of ionophores include crown ether compounds such as those described in Bull. Chem. Soc. Japan, 1980, 53, 547 and U.S. Pat. No. 4,361,473, multiheteromacrocyclic compounds such as those described in U.S. Pat. Nos. 3,965,116 and 4,001,279, hemispherand compounds such as those described in EP-A-0 082 518 and U.S. Pat. No. 4,505,800, phenanthroline compounds such as those described in U.S. Pat. No. 3,483,112 and U.S. Ser. No. 187,175, filed Apr. 28, 1988, and organotin compounds such as those described in published European Patent Application No. 88309588.7.

Preferably, a chain of from 4 to 15 atoms separates the ionophore group from the backbone of the cross-linkable polymer. The chain may comprise an alkylene group. A particularly preferred chain comprises an alkylene group having from 2 to 10, more preferably from 5 to 10, carbon atoms.

The radiation-sensitive composition of the invention is preferably film-forming. Also, it is very desirable for the composition to be solvent-soluble so that a film of the polymer can be coated from solution. Crosslinking of the composition by exposure to activating radiation will preferably render the polymer solvent-insoluble. Preferred solvents are salt-free aqueous solvents or common organic solvents e.g. acetone, tetrahydrofuran, dimethylformamide, benzene and toluene.

The radiation-crosslinkable polymer may be an addition polymer produced by the free radical polymerisation of ethylenically unsaturated monomers. For example, the recurring units having an ionophore group and the recurring units having a crosslinking group may be derived from an ethylenically unsaturated carboxylic acid or anhydride (e.g. acrylic acid, methacrylic acid and maleic anhydride), a vinyl ester (e.g. vinyl acetate), styrene, a vinyl ether (e.g. methyl vinyl ether), a vinyl ketone (e.g. methyl vinyl ketone) or a vinyl amine (e.g. vinyl imidazole and vinyl pyrrolidone).

Preferably, the radiation-crosslinkable polymer further comprises recurring units of an inert diluent monomer. The diluent monomer may be selected to provide the crosslinkable polymer with desired physical properties particularly with regard to film-forming ability, hardness and solubility. A diluent monomer may be selected from the monomers listed above from which the recurring units having crosslinking groups and ionophore groups, respectively, may be derived. The diluent monomer is chosen so that it is free of groups which would interfere with the function of the crosslinking and ionophore groups. Specific examples of suitable diluent monomers include the alkyl acrylates and methacrylates e.g. methyl methacrylate.

The radiation-crosslinkable polymer may consist solely of recurring units having an ionophore group and recurring units having a crosslinking group each present in an amount from 1 to 99 mole percent. Preferably, the polymer contains recurring units derived from a diluent monomer in an amount up to 98 mole percent. More preferred compositions will depend on the monomers used and the desired properties of the polymer. Typically, preferred polymers comprise at least 50 mole percent recurring units derived from a diluent monomer, up to 20 mole percent recurring units having an iopophore group and up to 30 mole percent recurring units having a crosslinking group.

The radiation-crosslinkable composition of the invention is suitable for use in the preparation of ion-sensitive electrochemical sensors, particularly those having an ion-sensitive membrane coated on a surface thereof. When used in the preparation of microelectronic sensors such as field effect sensors, the composition offers several advantages with regard to mass fabrication.

For example, ionophore deposition becomes an integral part of the wafer fabrication process. This would be done photolithographically by exposure of the coated wafer through a mask. Further, the use of a sequence of different compositions and appropriate masks would facilitate the fabrication of multiple ion sensors. The overriding advantage of the composition is that it enables the imagewise deposition of the ionophore where it is required i.e. on the sensor device gate at the pre-cut wafer stage.

The membrane may be prepared by first forming a solution of the composition and, if desired, a plasticizer in a suitable solvent e.g. acetone. The solution is coated on a surface of the sensor e.g. by dipping or spraying, and the solvent is evaporated to form the membrane. Slow evaporation of the solvent is preferred to avoid the formation of pinholes in the membrane.

Preferably, the membrane is made as thin as possible to provide the optimum response time. When preparing ion-sensitive field effect transistors (ISFETS) thicknesses of from 2 to 10 $\mu$m, preferably from 3 to 7 $\mu$m are preferred.

The present electrochemical sensors may be used to determine the concentration of ionic species in solution. For example, they may be used to determine the concentration of cations, e.g., sodium ions. The sensor may be contacted with the solution to be tested and the ion activity determined as a function of the potential generated between the sensing electrode and a reference electrode.

The invention is further illustrated with reference to the accompanying drawings.

FIG. 1 shows in cross-section an ISFET device comprising a semiconductor substrate 10 made of silicon having a p-type doping polarity. Two separate diffusion regions 11 and 12 having an n-type doping polarity (n+) are located in the semiconductor substrate at the upper surface thereof. Diffusion region 12 is referred to as the source while diffusion region 11 is referred to as the drain. The diffusion regions are each about 1 or 2 $\mu$m in depth, have a length of about 400 $\mu$m and are spaced about 20 $\mu$m apart. When the device is in use, a conducting channel 21 exists between the two diffusion regions. The channel is lightly-doped n-type (n$^-$) to provide a depletion mode device.

The surface of the semiconductor substrate 10 between the two diffusion regions is known as the gate. An electrically-insulating layer 13 of silicon dioxide covers the surface of the substrate 10 and is itself covered by a layer 14 of silicon nitride. The insulator material between the two diffusion regions is known as the gate insulator.

Aluminum layers 15 and 16 are deposited on the source diffusion region and the drain diffusion region, respectively, to provide electrical contacts therewith.

An ion-sensitive polymeric membrane 17 is deposited over the insulating layers 13 and 14 above the gate region of the device. An encapsulating layer 18 comprising layers of an epoxy resin and polyimide covers the electrical contacts to the source and the drain to shield them from a solution to be analyzed.

FIG. 1 shows the ISFET in use. The ion-sensitive membrane 17 is in contact with a solution 19 to be analysed which contains ions to which the membrane is sensitive. A reference electrode 20 coupled to a voltage source is provided in the solution. A voltage source is also provided between the source diffusion region and the drain diffusion region to establish a potential difference sufficient to cause current flow in the conducting channel 21 between the diffusion regions.

Ions in the solution 19 interact with the ion-sensitive membrane to produce a potential difference between the solution and the membrane, thereby creating an electric field in the conducting channel 21. The strength of the electric field depends on the concentration of ions in solution and controls the magnitude of the current flowing through the conducting channel, i.e., the drain current.

In order to determine the response of the ISFET to various concentrations of ions using the method illustrated in FIG. 1, a current must be made to flow between the source and the drain. This is accomplished by applying a voltage, e.g., 1 volt, to the drain. The magnitude of the drain current is set by applying a constant voltage e.g. 12 volts to a variable resistor 22, e.g., 120 k ohm. The operational amplifier, working in inversion, is used to apply a potential to the gate of the device, via the reference electrode and the solution, such that a current equal and opposite to the drain current flows through the device. On exposure to solution, electrochemically induced potential changes occur thus tending to cause drain current changes. Under these conditions, the operational amplifier will change the potential applied in order to offset the electrochemically induced voltage changes and hence maintain the drain current. Thus, the amplifier output ($v_{out}$) varies in accordance with the concentration of ions in solution and a plot of applied gate potential against ion activity provides a calibration curve for the ISFET.

The invention is further illustrated by way of example as follows.

EXAMPLE 1

Preparation of poly-co(methylmethacrylate-methacrylic acid-methacryloyloxymethylbenzo-15-crown-5)

Methyl methacrylate (26 mmoles, 2.60 g), methacrylic acid (3.25 mmoles, 0.28 g), 4'-methacryloyloxymethylbenzo-15-crown-5 (2.02 mmoles, 0.72 g), azobisisobutyronitrile (0.12 mmoles, 0.02 g) and ethanol (160 ml) were placed in a three-necked 500 ml round-bottomed flask, fitted with a nitrogen inlet and a water condenser. To minimize oxygen inhibition, the ethanol solvent was bubbled with nitrogen for 30 mins immediately before use, and a nitrogen blanket was maintained throughout the course of the reaction. The reaction mixture was stirred for 20 hours at 60° C. At the end of this period, the polymer was precipitated into diethyl ether, filtered off and dried in a vacuum overnight. The yield was 0.73 g (20.2%). NMR spectroscopy indicated that the resultant polymer incorporated the monomer units methyl methacrylate, methacrylic acid and 4'-methacryloyloxymethylbenzo-15-crown-5 in the molar ratio 8.3:1.0:2.1, i.e. the crown ether monomer unit was present at a level of 18.4 mole percent.

The addition of benzene chromium tricarbonyl yielded a radiation-sensitive composition of the invention.

EXAMPLE 2

Preparation of poly(methylmethacrylate-N-methacrylamido-6-caproic acid-N-methacrylamido-6-caproyloxy-methylbenzo-15-crown-5)

Following the procedure given in the previous preparation, a polymer was prepared from the following mixture: methyl methacrylate (3.0 g), N-methacrylamido-6-caproic acid(0.1 g), N-methacrylamido-6-aminocaproyloxymethylbenzo-15-crown-5 (0.2 g), ethanol (190 ml), acetone (30 ml) and azobisisobutyronitrile (0.02 g). The yield was 1.1 g (33%). NMR spectroscopy indicated that the polymer incorporated the monomer units in the molar ratio 36.2:1.0:2.0 i.e. the crown ether monomer unit was present at a level of 5 mole percent.

The addition of benzene chromium tricarbonyl yielded a radiation-sensitive composition of the invention.

EXAMPLE 3

Preparation of poly-co(methylmethacrylate-1-vinylimidazole-4'-methacryloyloxymethylbenzo-15-crown-5) quaternized with chloromethylcarbonyloxyethylmethacrylate 1-Vinylimidazole (3.76 g), azobisisobutyronitrile (0.05 g), ethanol (60 ml) and acetone (20 ml) were placed in a three-necked round-bottomed flask. The flask was equipped with a condenser, a nitrogen inlet and a syringe pump tubing inlet. Methyl methacrylate (8.80 g), 4'-methacryloyloxymethylbenzo-15-crown-5 (2.22 g), ethanol (30 ml) and acetone (5 ml) were placed in a 50 ml syringe. The contents of the syringe were added to the flask at 60 ml/hr, the flask contents being stirred and maintained at 60° C. A nitrogen blanket was maintained throughout the reaction which was allowed to proceed for 16 hours after completing the addition. The polymer was then recovered by precipitation into diethyl ether. The yield was 7.21 g (48.8%). NMR spectroscopy indicated that the resultant polymer incorporated the monomer units methylmethacrylate, 1-vinylimidazole, and 4'-methacryloyloxymethylbenzo-15-crown-5 in the molar ratio 25.1:11.3:2.0 i.e. the crown ether monomer unit was present at a level of 5.2 mole percent.

The quaternization of such a polymer was carried out as follows. The polymer (1 g) and the quaternizing agent chloromethylcarbonyloxyethyl methacrylate were dissolved in dimethylformamide (50 ml) and placed in a vessel for 20 hours at 80° C. with 0.1 g of catalyst (Topanol OC) present. The product was precipitated into ethylacetate and then dried under vacuum.

The addition of a photopolymerisation initiator comprising a ketocoumarin and an amine yielded a radiation-sensitive composition of the invention.

EXAMPLE 4

Preparation of the addition product of poly(styrenemaleic anhydride) and (2-hydroxyethylthio)tri-n-butyltin A polymer was prepared from the following mixture: styrene (25 ml), maleic anhydride (24 ml), 1,4-dioxan (400 ml) and azobisisobutyronitrile (0.2 g). The reaction temperature was 70° C. and the reaction was allowed to proceed for four hours. The resultant polymer was precipitated into diethyl ether, filtered off and then dried under vacuum. NMR spectroscopy indicated that the polymer incorporated the monomer units in the molar ratio 1:1.

The ionophore was attached to the polymer backbone by refluxing the following mixture of 80° C. for 12 hours: poly(styrene-maleic anhydride) (2 g), (2-hydroxyethylthio)tri-n-butyltin (6 g) and benzene (50 ml). The reaction yielded a modified copolymer in which the addition of the tin compound to the maleic anhydride unit was virtually quantitative i.e. 1:1. The ring-opening of each maleic anhydride unit provided a pendant carboxyl group and a pendant (carboxyethylthio)tri-n-butyltin group.

A radiation-sensitive composition was prepared by dissolving the ionophore-containing polymer and benzene chromium tricarbonyl in acetone. A thin film of the composition was exposed to UV light and crosslinking occurred in the exposed area.

EXAMPLE 5

The polymer of Example 2 (0.05 g) and benzene chromium tricarbonyl (0.001 g) were dissolved in acetone (2.5 ml). The solution was diluted with acetone (10 ml) and one drop of the resulting solution was applied to the gate region of a field effect transistor of the type shown in FIG. 1. After allowing the solvent to evaporate, crosslinking was effected by irradiating the device with UV light for five minutes. Irradiation was performed in an exposure frame that consisted of four 125 W medium pressure mercury vapour lamps set at a distance of 45 cm from the exposure surface. This procedure was found to give a field effect sensor having a coherent ion-sensitive gate membrane.

The response characteristics of the field effect sensor were measured following the procedure outlined with regard to FIG. 1. An automatic burette was used to dispense aliquots of a concentrated sodium ion solution into a known volume of distilled water to produce a range of standard solutions to be measured. A remote Ag/AgCl reference electrode with a 0.1M nitrate bridge was used to complete the electrochemical cell. The potential was recorded when a drift of less than 0.4 mV per minute was obtained.

Figure 2:
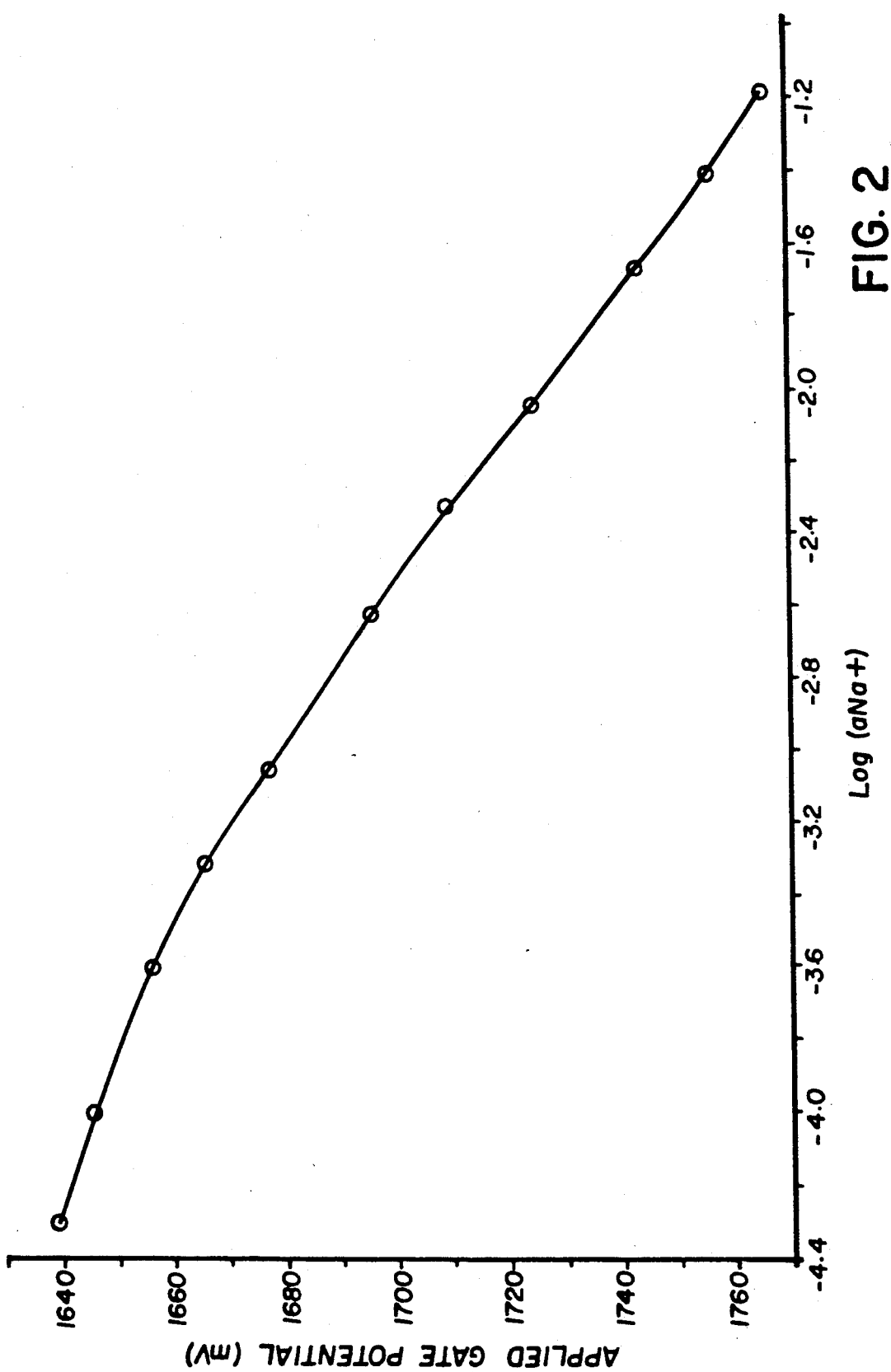
FIG. 2 is a graph showing the response of an ISFET of the invention to various concentrations of sodium ion.

The field effect sensor was operated at a constant drain current (100 microamps). The potential needed to offset chemically induced potential changes at the membrane, and hence maintain the drain current, was determined. The results shown in Table I and in FIG. 2 indicate that good response characteristics were obtained.

TABLE I

| | |
|---|---|
| Slope (mV/decade) | −49.50 |
| Linear range (Log [aNa$^+$]) | −2.63 to > −1.19 |
| Limit of detection (Log [aNa$^+$]) | < −3.76 |
| Correlation coefficient | 1.00 |

The invention has been described in detail with particular reference to preferred embodiments thereof, but it will be understood that variations and modifications can be effected within the spirit and scope of the invention.

What is claimed is:

1. A radiation-sensitive composition comprising a radiation-crosslinkable polymer wherein the polymer comprises recurring units having an ionophore group which selectively entrains an ion and recurring units having a crosslinking group.

2. A composition according to claim 1 wherein the crosslinking group is a nucleophilic group and the composition contains a radiation-sensitive transitional metal carbonyl compound.

3. A composition according to claim 1 wherein the crosslinking group is an ethylenically unsaturated group and the composition contains a photopolymerization initiator.

4. A composition according to claim 1 wherein the ionophore group is a crown ether.

5. A composition according to claim 1 wherein the radiation crosslinkable polymer is an addition polymer derived from the free radical polymerization of ethylenically unsaturated monomers.

6. A composition according to claim 5 wherein the recurring units having an ionophore group and the recurring units having a crosslinking group are each, independently, derived from monomers selected from an ethylenically unsaturated carboxylic acid or anhydride, a vinyl ester, styrene, a vinyl ether, a vinyl ketone or a vinyl amine.

7. A composition according to claim 5 wherein the radiation-crosslinkable polymer further comprises recurring units of a diluent monomer free of groups which interfere with function of the ionophore and crosslinking groups.

8. A composition according to claim 7 wherein all the recurring units of the radiation-crosslinkable polymer are derived from an ethylenically unsaturated carboxylic acid.

9. A method of preparing a crosslinked ion-sensitive composition which method comprises exposing to activating radiation a radiation-sensitive composition according to any one of claims 1 to 8 inclusive.

10. A method of preparing an electrochemical sensor having an ion-sensitive membrane which method comprises coating a surface of the sensor with a radiation-sensitive composition according to any one of claims 1 to 8 inclusive, exposing to activating radiation the area of the coated surface where the membrane is required in order to crosslink the composition in that area and removing any non-exposed portions of the composition from the surface.

11. A composition according to claim 1 wherein said ionophore is a member selected from the group consisting of crown ether compounds, multiheteromacrocyclic compounds, hemisperand compounds, phenanthroline compounds, and organotin compounds.

* * * * *